United States Patent
Benkert et al.

(10) Patent No.: US 12,315,044 B2
(45) Date of Patent: May 27, 2025

(54) DEEP LEARNING-BASED REALTIME RECONSTRUCTION

(71) Applicant: Siemens Healthineers AG, Forchheim (DE)

(72) Inventors: Thomas Benkert, Neunkirchen am Brand (DE); Marcel Dominik Nickel, Herzogenaurach (DE); Simon Arberet, Princeton, NJ (US); Boris Mailhe, Plainsboro, NJ (US); Mahmoud Mostapha, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 600 days.

(21) Appl. No.: 17/473,229

(22) Filed: Sep. 13, 2021

(65) Prior Publication Data

US 2023/0084413 A1    Mar. 16, 2023

(51) Int. Cl.
*G06T 11/00* (2006.01)
*G06N 3/08* (2023.01)
*G16H 30/20* (2018.01)

(52) U.S. Cl.
CPC .............. *G06T 11/003* (2013.01); *G06N 3/08* (2013.01); *G16H 30/20* (2018.01); *G06T 2210/41* (2013.01)

(58) Field of Classification Search
CPC ... G06T 11/00; G06T 11/003; G06T 2210/41; G06N 3/08; G06N 3/045; G06N 3/0464; G06N 3/0442; G06N 3/084; G16H 30/20; G16H 40/67
See application file for complete search history.

(56) References Cited

U.S. PATENT DOCUMENTS

| | | | |
|---|---|---|---|
| 8,508,226 B2 | 8/2013 | Feiweier et al. | |
| 9,113,810 B2 * | 8/2015 | Edelman | A61B 5/004 |
| 9,714,998 B2 * | 7/2017 | Krueger | G01R 33/5676 |
| 10,495,717 B2 * | 12/2019 | Hoge | G01R 33/5616 |
| 11,182,895 B2 * | 11/2021 | Honkala | A61B 6/5211 |
| 11,300,645 B2 * | 4/2022 | Schlemper | G06V 10/768 |
| 11,328,394 B1 * | 5/2022 | Kim | G06T 5/60 |
| 11,734,817 B2 * | 8/2023 | Takeshima | G16H 10/60 705/2 |

(Continued)

FOREIGN PATENT DOCUMENTS

CN    108896943 B  *  6/2020  ......... G01R 33/4818

OTHER PUBLICATIONS

Dang, Jun, et al. "Simultaneous 4D-CBCT reconstruction with sliding motion constraint." Medical physics 43.10 (2016): 5453-5463. (Year: 2016).*

*Primary Examiner* — Stephen R Koziol
*Assistant Examiner* — Benedict E Lee

(57) ABSTRACT

For reconstruction, a machine-learned model is adapted to allow for reconstruction based on the repetitions available in some scanning. The reconstruction for one or more subsets is performed during the scanning. The machine-learned model is trained to reconstruction separately or independently for each repetition or to use information from previous repetitions without requiring waiting for completion of scanning. The reconstructed image may be displayed much more rapidly after completion of the acquisition since the reconstruction begins during the reconstruction.

20 Claims, 4 Drawing Sheets

(56) References Cited

U.S. PATENT DOCUMENTS

| | | | | |
|---|---|---|---|---|
| 11,763,134 | B2* | 9/2023 | Chen | G06N 3/045 |
| | | | | 706/15 |
| 11,816,832 | B2* | 11/2023 | Tang | G06T 11/005 |
| 12,067,651 | B2* | 8/2024 | Tang | G06N 3/08 |
| 2015/0247909 | A1* | 9/2015 | Wawro | A61B 5/055 |
| | | | | 600/420 |
| 2018/0018757 | A1* | 1/2018 | Suzuki | G06N 3/045 |
| 2019/0059780 | A1* | 2/2019 | Lee | G06T 7/0014 |
| 2019/0366124 | A1* | 12/2019 | Berlinger | G06T 7/74 |
| 2020/0003858 | A1* | 1/2020 | Takeshima | G01R 33/5608 |
| 2020/0294287 | A1* | 9/2020 | Schlemper | G06T 3/60 |
| 2021/0059609 | A1* | 3/2021 | Zhang | A61B 6/037 |
| 2021/0295501 | A1* | 9/2021 | Hu | G06T 7/11 |
| 2022/0067986 | A1* | 3/2022 | Takeshima | G01R 33/5608 |
| 2022/0172410 | A1* | 6/2022 | Wheaton | G06T 11/005 |
| 2022/0179030 | A1* | 6/2022 | Tian | A61B 5/055 |
| 2022/0208355 | A1* | 6/2022 | Li | G06T 7/174 |
| 2023/0022425 | A1* | 1/2023 | Prevrhal | A61B 6/527 |
| 2023/0059132 | A1* | 2/2023 | Li | G06N 3/088 |
| 2023/0014745 | A1* | 3/2023 | Chen | G06N 3/08 |
| 2023/0335274 | A1* | 10/2023 | Bychkov | G16H 40/67 |

* cited by examiner

DEEP LEARNING-BASED REALTIME RECONSTRUCTION

FIELD

This disclosure relates to medical image reconstruction, such as reconstruction in magnetic resonance (MR) imaging.

BACKGROUND

Some protocols for scanning a patient in medical imaging, such as MR, computed tomography (CT), positron emission tomography (PET), or single photon emission computed tomography (SPECT), use repetitious scanning. In MR, multiple repetitions are commonly acquired in diffusion-weighted imaging or turbo-spin-echo imaging, where images reconstructed from each repetition are averaged to decrease the level of noise in the final image. Repetition is also performed in the acquisition of multiple contrasts, for example when acquiring images with different echo times or different flip angles.

MR image reconstruction, such as reconstruction using a deep-learned neural network, can be computationally very demanding. These reconstructions often rely on processing data with several iterations and/or multiple mathematical operations, such as many convolutions and evaluation of a cost function. The corresponding reconstruction times can be quite long. Usually, image reconstruction is started after the end of the respective acquisition when all data (e.g., slices, repetitions, averages, . . . ) have been collected. Therefore, the entire reconstruction time is noticeable for the user as the user must wait for both the completed acquisition and subsequent reconstruction. This can be cumbersome for a clinical workflow.

To enable clinically acceptable reconstruction times, performance improvements of the reconstruction itself are often employed. For example, specialized hardware is used to provide parallelization across different CPU/GPU cores or computing on a GPU. As another example, the reconstruction algorithm is altered to provide more efficient implementation of the required operations. However, even with these improvements, there is still an overhead in time for reconstruction after acquisition, which undesired overhead may be annoying to the user.

SUMMARY

By way of introduction, the preferred embodiments described below include methods, systems, instructions, and computer readable media for reconstruction. A machine-learned model is adapted to allow for reconstruction based on the subsets available in some scanning. The reconstruction for one or more subsets is performed during the scanning. The machine-learned model is trained to reconstruction separately or independently for each subset or to use information from previous subsets without requiring waiting for completion of scanning. The reconstructed image may be displayed much more rapidly after completion of the acquisition since the reconstruction begins during the reconstruction.

In a first aspect, a method of reconstruction is provided for a medical imaging system. The medical imaging system scans the patient. The scanning acquires first and second subsets of scan data in sequence. An object of the patient is first reconstructed from the first subset of the scan data before completion of the scanning of the patient for the second subset of the scan data. The first reconstructing is by, at least in part, a machine-learned model. The machine-learned model has an architecture for separate reconstruction of the first and second subsets. The object is second reconstructed from the second subset of the scan data. The second reconstruction is by, at least in part, the machine-learned model. An image of the object is generated from the first reconstruction from the first subset and from the second reconstruction from the second subset.

In one embodiment, the scanning is magnetic resonance scanning pursuant to a diffusion-weighted, turbo-spin-echo, contrast with different echo times, contrast with different flip angles protocol, contrast with different b-values, or contrast with different averages. The protocol is for scanning the patient in a single imaging appointment. The scanning may include scanning for any number (e.g., three or more) subsets where the first and second subsets are temporally adjacent subsets in the sequence. The first reconstructing completes prior to the completion of the scanning for the second subset.

The machine-learned model, such as the architecture, is designed for the separate reconstruction in one or more of various ways. In one approach, the architecture is designed to independently reconstruct for the first and second subsets. In another approach, the machine-learned model was trained for the separate reconstruction using a loss based on aggregation across training subsets. Where the reconstructed images are then combined, one of the first and second reconstructions may be motion corrected relative to the other of the first and second reconstructions prior to combination.

The architecture may be designed for sharing of information during application. In one approach, the architecture includes a temporal network relating the first subset to the second subset. For example, the temporal network is a recurrent neural network, a gated recurrent unit, or a long-short term memory. In another approach, the architecture includes different parts where one or more of the parts are performed for the first reconstructing without the second subset and one or more parts are performed after acquiring the second subset. In yet another approach, the architecture is a conditional reconstruction model configured to receive historical information. For example, the historical information are values for latent variables from application of the machine-learned model to a previous subset such that the machine-learned model uses the values from the first reconstructing for the second reconstructing.

In another embodiment, the medical imaging system is controlled to cease scanning based on the second reconstruction. The reconstruction by subset may be used to determine during the scanning whether additional subsets are to be acquired.

In some embodiments, the image is displayed in an amount of time after completion of the second reconstructing that is less than a time to reconstruct from both the first and second subsets. Instead of 30 seconds to 1 minute wait for reconstruction once all the subsets are acquired, the reconstruction takes 10 seconds or less after completion of the scanning since the reconstruction for one or more subsets has already started or completed during the scanning.

In a second aspect, a system is provided for reconstruction in medical imaging. A medical scanner is configured to scan a region of a patient. The scan provides scan data in different subsets. An image processor is configured to reconstruct a representation of the region separately for each of the subsets. The image processor is configured to reconstruct by application of a machine-learned model that uses information from a previous reconstruction in a later reconstruction.

A display is configured to display an image of the region from a combination of the representations from the different subsets.

In various embodiments, the machine-learned model includes a temporal network that uses the information, the machine-learned model includes inputs for the subsets and includes a part combining the information, or the information is values of latent variables of the previous reconstruction.

As example scans, the scan is a contrast, diffusion-weighted, or turbo-spin-echo magnetic resonance scan.

In a third aspect, a system is provided for reconstruction in medical imaging. A medical scanner is configured to scan a region of a patient, the scan providing scan data in different subsets. An image processor is configured to reconstruct a representation of the region separately for each of the subsets. The image processor is configured to reconstruct by application of a machine-learned model where the representation for one of the subsets is reconstructed prior to completion of the scan for another of the subsets. A display is configured to display an image of the region from a combination of the representations from the different subsets.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

In some medical imaging protocols, repetition is used to collect, at least in part, redundant information. These repetitions, averages, or contrasts are referred to as repetitions or subsets. Where the acquisition of each subset is not spread over the entire acquisition but is finished earlier, the image reconstruction for this subset can be performed right after the acquisition of this subset is completed and while the acquisition of any other or subsequent subset(s) is still ongoing. Hard-coded "conventional" reconstructions, such as image registration of different b-values and diffusion directions in the context of eddy current correction for diffusion weighted imaging, may use sequential reconstruction by subset but any machine-learned model is not adapted to this approach. For conventional integrations of deep learning-based reconstructions, reconstruction is usually only triggered after end of image acquisition. In the approach used herein, the acquisition time itself can be used for image reconstruction.

Reconstruction during scanning significantly reduces the user-noticeable reconstruction time. Such seemingly short reconstruction times after completion of scanning are desirable for clinical routine. Given the time savings by reconstructing, at least in part, during scanning, even more computationally demanding reconstructions, which—from a clinical point of view—would be prohibitive otherwise, may be used. Performance optimizations or improvements, such as through hardware or coding optimization, might become less relevant, saving coding time and expense.

A final image or images processed with a computationally demanding reconstruction may be available with little or no visible overhead for the operator (i.e., directly or with only a short delay (e.g., 1-5 seconds, 10 seconds or less, or other period faster than possible if waiting to collect all data before reconstruction) after end of image acquisition. Preliminary images may be generated and displayed while still scanning. Images from subsets before completion of the scanning may be displayed until the final image based on reconstruction from all the subsets or after completion of scanning is displayed.

Figure 1:
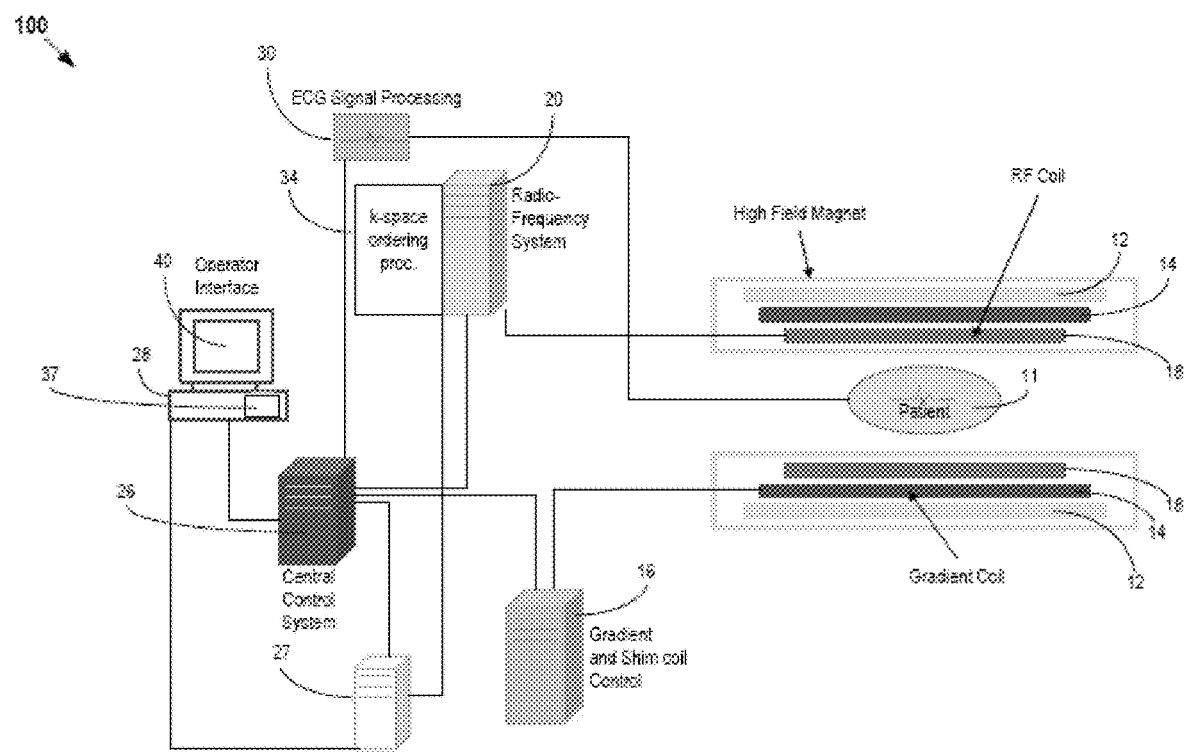
FIG. 1 is a block diagram of an embodiment of an MR system for medical imaging with reconstruction from the subsets.

FIG. 1 shows one embodiment of a system for reconstruction in medical imaging. The system scans a given patient using a given protocol, creating repetitions or subsets of scan data having redundant information. The system applies a machine-learned model in reconstruction where the model is designed to provide for reconstruction by subset. The system is described below in general, with a following method providing other details. The system implements the method of FIG. 3 or another method.

The example used herein is in a MR context (i.e., a MR scanner), but redundant scanning protocols and corresponding types of scanner may be used in reconstruction for CT, PET, SPECT, or other medical imaging.

The system uses a machine-learned model in reconstruction. The machine-learned model is formed from one or more networks and/or another machine-learned arrangement (e.g., support vector machine). For example and used herein, the machine-learned model is a deep-learned neural network. The machine-learned model is used for at least part of the reconstruction, such as regularization of reconstruction. In regularization, image or object domain data is input, and image or object domain data with less artifact is output. The remaining portions or stages of the reconstruction (e.g., Fourier transform and gradients in iterative optimization) are performed using reconstruction algorithms and/or other machine-learned networks. In other embodiments, the machine-learned model is used for all the reconstruction operations (one model to input k-space data and output regularized image data) or other reconstruction operations (e.g., used for transform, gradient operation, and/or regularization). The reconstruction is of an object or image domain from projections or measurements in another domain, and the machine-learned model is used for at least part of the reconstruction.

The system is implemented by an MR scanner or system, a computer based on data obtained by MR scanning, a server, or another processor. MR scanning system 100 is only exemplary, and a variety of MR scanning systems can be used to collect the MR data. The MR scanner 100 is configured to scan a patient. The scan provides scan data in a scan domain. The system 100 scans a patient to provide k-space measurements (measurements in the frequency domain). In a given scan or examination (e.g., imaging appointment), the patient is scanned multiple times as part of a protocol providing repetitions or groups of at least partly redundant information.

In the system 100, magnetic coils 12 create a static base magnetic field in the body of patient 11 to be positioned on a table and imaged. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generate magnetic field pulse sequences.

RF (radio frequency) module 20 provides RF pulse signals to RF coil 18, which in response produces magnetic field pulses that rotate the spins of the protons in the imaged body of the patient 11 by ninety degrees, by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image (i.e., for reconstruction in the object domain from the k-space data in the scan domain). In some embodiments, the image data processor is in or is the central control unit 26. In other embodiments, such as the one depicted in FIG. 1, the image data processor is in a separate unit 27. ECG synchronization signal generator 30 provides ECG signals used for pulse sequence and imaging synchronization. A two- or three-dimensional k-space storage array of individual data elements in k-space component processor unit 34 stores corresponding individual frequency components forming an MR dataset. The k-space array of individual data elements has a designated center, and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired using a Cartesian acquisition strategy as the multiple individual frequency components are sequentially acquired during acquisition of an MR dataset representing an MR image. A storage processor in the k-space component processor unit 34 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array, and magnetic field gradient change between successively acquired frequency components is substantially minimized.

The central control unit 26 uses information stored in an internal database to process the detected MR signals in a coordinated manner to generate high quality images of a selected slice(s) of the body (e.g., using the image data processor) and adjusts other parameters of the system 100. The stored information includes a predetermined pulse sequence of an imaging protocol and a magnetic field gradient and strength data as well as data indicating timing, orientation, and spatial volume of gradient magnetic fields to be applied in imaging.

The medical scanner 100 is configured by the imaging protocol to repetitively scan a region of a patient 11. The same patient 11, without leaving the scanner 100, is scanned in a repetitive manner, providing scan data in subsets based on the protocol. For example, in MR, such protocols for scanning a patient for a given examination or appointment include diffusion-weighted imaging (acquisition of multiple b-values, averages, and/or diffusion directions), turbo-spin-echo imaging (acquisition of multiple averages), contrast imaging with different echo times, contrast imaging with different flip angles, contrast with different b-values, or contrast with different averages. For these or other sequences, protocols, or acquisition types, the acquisition acquires different subsets of data, such as acquisition of several slices, averages, repetitions, contrasts, b-values, diffusion directions, cardiac phases, or other at least partly redundance information. Other types of MR or non-MR protocols may use repetition or subsets. The sequential or other scanning results in a set of scan data grouped as two or more subsets or scans.

The central control unit 26 (i.e., controller) and/or processor 27 is an image processor that reconstructs a representation of the patient from the k-space data. The image processor is a general processor, digital signal processor, three-dimensional data processor, graphics processing unit, application specific integrated circuit, field programmable gate array, artificial intelligence processor, digital circuit, analog circuit, combinations thereof, or another now known or later developed device for reconstruction. The image processor is a single device, a plurality of devices, or a network. For more than one device, parallel or sequential division of processing may be used. Different devices making up the image processor may perform different functions, such as reconstructing by one device and volume rendering by another device. In one embodiment, the image processor is a control processor or other processor of the MR scanner 100. Other image processors of the MR scanner 100 or external to the MR scanner 100 may be used.

The image processor is configured by software, firmware, and/or hardware to reconstruct. The image processor operates pursuant to instructions stored on a non-transitory medium to perform various acts described herein.

The image processor is configured to reconstruct a representation in an object domain. The object domain is an image space and corresponds to the spatial distribution of the patient. A planar or volume representation or object is reconstructed as an image representing the patient. For example, pixels values representing tissue in an area or voxel values representing tissue distributed in a volume are generated.

The representation or object in the object domain is reconstructed from the scan data in the scan domain. The scan data is a set or frame of k-space data from a scan of the patient. The protocol for a scan of a patient may generate multiple such subsets or frames of k-space (scan) data. For each subset, the k-space measurements resulting from the scan sequence are transformed from the frequency domain to the spatial domain in reconstruction. In one approach, reconstruction for a given subset is an iterative process, such as a minimization problem. In some embodiments, an unrolled iterative reconstruction is provided as alternating gradient updates and regularization where a network is provided for regularization through iteration sequences. A given iteration either in an unrolled network or through a repetition of the reconstruction operations includes a gradient update and regularization. The gradient update compares the current image object with the scan data (e.g., k-space measurements). This comparison uses a system transform to relate the measurements to the image object. Any gradient or comparison relating the image object to the measurements may be used. Regularization is provided in one, some, or all the iterations and can include the application of a network. Other filtering and/or operations for reconstruction and/or post-reconstruction may be provided. Input bias field correction and/or extrapolation for momentum may be provided as part of the reconstruction. In other embodiments, the reconstruction is performed without iteration.

A representation is reconstructed separately for each of the subsets. The reconstruction for each subset may be independent of other subsets or respective reconstructions. Alternatively, the separate reconstruction uses information between subsets. The reconstruction for a later subset may or may not use information from an earlier subset, the reconstructing of the earlier subset, or the reconstructed object of the earlier subset. A different representation of the object is reconstructed for each subset. In other embodiments, part of the reconstruction is performed separately for subsets with other parts of the reconstruction using information from multiple subsets.

Using one of various approaches, the machine-learned model is designed for reconstruction by subset. Separate reconstruction of subsets is enabled through the design of the applied network or machine-learned model.

In one approach, separate and independent reconstruction uses a same machine-learned model applied at different times or as different instances to the different subsets, providing representations of the object from the different subsets. The machine-learned model may have been trained using a loss and ground truth based on subsets. Different models with the same architecture may be trained for the different subsets or one model is trained to be applied to all the subsets.

In another approach, the machine learning and corresponding architecture couples information between subsets in the training phase but not the application phase. For example, the one machine-learned model is trained to be applied to the different subsets using a loss based on aggregation across the subsets, providing information linkage or coupling between subsets in training. The reconstruction for one or more subsets uses application of a machine-learned model having been trained for the reconstruction for each of the repetitions based on a loss function between an aggregate of outputs from the repetitions of the protocol and a ground truth image. The training of the machine-learned model results in values for learnable (learned) parameters. By using the loss based on the aggregate image, object, or representation across subsets to train the machine-learned model for reconstruction of a subset, different values of the machine-learned model result than if a different loss where used. The same machine-learned model is sequentially or in parallel applied in reconstruction for the different subsets resulting from the imaging protocol. While the training used an aggregation across subsets (e.g., average image from the different repetitions) for loss, the machine-learned model is applied to reconstruct the image for a given one of the subsets or sub-group of subsets at a time.

In other approaches, the coupling of information between subsets occurs on the application or testing phase of the machine-learned model. Information from reconstruction of one subset is used in reconstruction of another subset. The machine-learned model uses information from a previous reconstruction in a later reconstruction. These approaches may include a temporal network (e.g., recurrent neural network) in or as the machine-learned model. The temporal network uses information from one or more previous reconstructions of a respective one or more subsets in reconstruction of a current subset. These approaches include a machine-learned model with different parts, one or more of which provide for reconstruction, at least in part, separately for subsets and one or more other parts that combine information from the one or more parts for separate operations to complete reconstruction or combine reconstructions. The approaches include a machine-learned model that uses values of latent variables (e.g., deep learned features) from reconstruction of one subset in the reconstruction of another subset. The initial reconstruction for any of these application-coupled approaches may use default or filler information as the coupled input not otherwise available.

In these approaches, the image processor is configured to reconstruct the representation (e.g., image or object) for each subset. The machine-learned model is used for one, some, or each reconstruction from respective subsets. The result is a set of reconstructed representations of the same region or partial reconstructions. The image processor is configured to combine the representations or complete the reconstruction from the partial reconstructions. Any motion correction and/or filtering may be used prior to combination. The aligned representations are combined to form one representation of the region of the patient. For example, the combination is a sum (e.g., average), a geometric mean, or a geometric product. The diffusion-weighted imaging and turbo-spin-echo imaging protocols sum or average the representations. The contrast protocol may use the geometric mean or product. Other combinations of representations from different repetitions may be used, such as based on the imaging protocol.

The resulting representation may be a complex or real image. The output image is the final reconstructed image. The output image represents the patient (i.e., a reconstructed representation). The image processor may be configured to generate an MR image from the combined representation. Where the representation is of an area, the values of the representation may be mapped to display values (e.g., scalar values to display color values) and/or formatted for display (e.g., interpolated to a display pixel grid). Alternatively, the output representation is of display values in the display format. Where the representation is of a volume, the image processor performs volume or surface rendering to render a two-dimensional image from the voxels of the volume. This two-dimensional image may be mapped and/or formatted for display as an MR image. Any MR image generation may be used so that the image represents the measured MR response from the patient. The image represents a region of the patient.

The image processor is configured to reconstruct for one of the subsets prior to completion of scanning for another of the subsets. For example, a representation is reconstructed using the machine-learned model for an initial subset prior to completing the scanning for the next temporally adjacent subset. The reconstruction may take longer than the subset scan, so the reconstruction for a subset may be complete prior to finishing scanning of another subsequent (i.e., not temporally adjacent) subset. In either case, the ability to perform at least part of reconstruction while scanning due to use of subsets allows for more rapid reconstruction once the scanning is complete.

Figure 2:
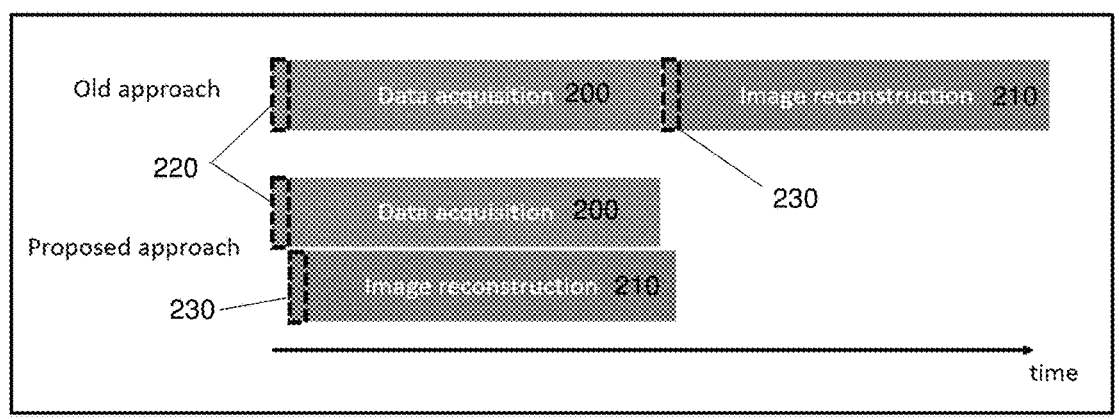
FIG. 2 illustrates reconstruction by subsets in real-time according to one embodiment.

FIG. 2 shows an example. In the old approach, all the data is first acquired at 200, and then image reconstruction is performed at 210. This may be the case even where the data is acquired in subsets (220 indicates an initial subset). The reconstruction 230 of the initial subset 220 using a machine-learned model occurs after completion of the data acquisition 200. In the proposed approach, the reconstruction 230 for the initial subset 220 occurs as soon as the initial subset 220 is acquired and before completion of the data acquisition 200 (and perhaps before completion of acquiring the immediately next subset). As a result, the image reconstruction 210 is completed shortly after completion of the complete data acquisition 200. For example, the image reconstruction takes 30-60 seconds. By reconstructing 210 during acquisition 200 due to use of subsets 220, the final image or reconstructed object is provided 1-5 or 1-10 seconds after completion of the scanning.

In other embodiments, the image reconstruction is not just one block but is multiple independent processing blocks, at least for computationally intensive processing where a post process combines the results. Each of the subsets or blocks 220 and corresponding reconstruction processing 230 is performed, with a following post-process to combine the results from the reconstruction processing blocks 230.

Where the acquisition of each subset is not spread over the entire acquisition but is finished earlier, the image reconstruction for each subset can be performed right after the acquisition of that subset is completed (i.e., while the acquisition of subsequent subsets is still ongoing). While this may be done for hard-coded reconstructions, such as image registration of different b-values and diffusion directions in the context of eddy current correction for diffusion weighted imaging, the design of the architecture of the machine learned model allows it to be done for deep learning-based reconstruction.

A generated image of the reconstructed representation (e.g., combined representation) for a given patient is presented on a display 40 of the operator interface. While images based on one or more but less than all the subsets may be displayed as reconstructed, the final image based on reconstruction from the entire data acquisition is displayed for diagnosis, prognosis, and/or therapy. The image is from a combination of the representations from the different subsets and represents the region of the patient.

The display 40 is a CRT, LCD, plasma, projector, printer, or other display device. The display 40 is configured by loading an image to a display plane or buffer. The display 40 is configured to display the reconstructed MR image of the region of the patient. The computer 28 of the operator interface includes a graphical user interface (GUI) enabling user interaction with central control unit 26 and enables user modification in substantially real time. The display processor 37 processes the magnetic resonance signals to provide image representative data for display on display 40, for example.

Figure 3:
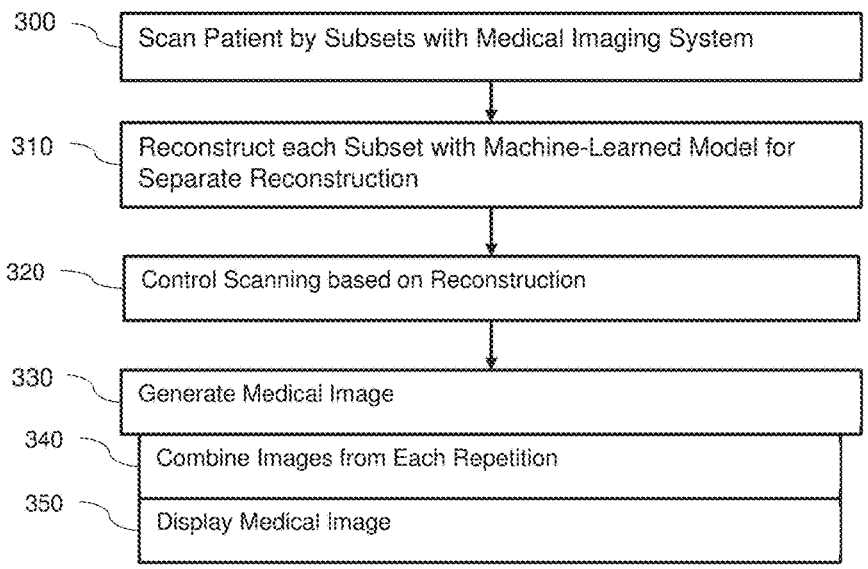
FIG. 3 is a flow chart diagram of one embodiment of a method for reconstruction using a machine-learned model designed for reconstruction with subsets.

FIG. 3 is a flow chart diagram of one embodiment of a method for reconstruction of a medical image in a medical imaging system, such as reconstruction of a MR image in an MR system. A machine-learned model as trained is applied for at least part of the reconstruction operation for each of multiple subsets of a scan of a patient following an imaging protocol. The application is part of scanning and reconstruction for patient diagnosis of a given patient for a given examination, scan, and/or appointment. The machine-learned model is used in reconstruction of a spatial representation from input k-space measurements for a patient. The machine-learned model has an architecture or design for use in reconstruction with subsets.

During application to one or more different patients and corresponding different scan data, the same learned weights or values of the machine-learned model are used. The model and values for the learnable parameters are not changed from one patient to the next, at least over a given time (e.g., weeks, months, or years) or given number of uses (e.g., tens or hundreds). These fixed values and corresponding fixed model are applied sequentially and/or by different processors to scan data for different patients. The model may be updated, such as retrained, or replaced but does not learn new values as part of application for a given patient.

The method is performed by the system of FIG. 1 or another system. The medical scanner scans the patient. An image processor reconstructs an object using the machine-trained model for each of the subsets. A display displays the medical image resulting from the reconstructions from the different subsets. Other components may be used, such as a remote server or a workstation performing the reconstruction and/or display.

The method is performed in the order shown or other orders. Additional, different, or fewer acts may be provided. For example, a preset, default, or user input settings are used to configure the scanning prior art act 300. As another example, the image is stored in a memory (e.g., computerized patient medical record) or transmitted over a computer network instead of or in addition to the display of act 340.

In act 300, the medical imaging system scans a patient. The scan is guided by a protocol, such as diffusion-weighted, contrast, or turbo-spin-echo protocol. The scanning results in measurements over a series of scans in the imaging protocol. The pulse or scan sequence repetitively scans the same region of the patient, resulting in subsets of scan data of the entire scan for a single imaging appointment. The subsets are sequentially acquired but some interleaving may be provided. Any number of subsets may be acquired as part of the scan, such as two or more (e.g., 3-12 subsets). Pairs of subsets are temporally adjacent where there is no intervening subset. The subsets may be independently or separately, or at least partly, reconstructed to represent that region.

In an MR example, a pulse sequence is created based on the configuration of the MR scanner (e.g., the imaging protocol selected such as diffusion-weighted, turbo-spin-echo, contrast with different echo times, contrast with different flip angles, contrast with different b-values, or contrast with different averages protocol). The pulse sequence is transmitted from coils into the patient. The resulting responses are measured by receiving radio frequency signals at the same or different coils. The scanning results in k-space measurements as the scan data. Scan data for different subsets is acquired. The scan includes scans for each subset or over a series of scans as part of the same instance of the protocol (i.e., same imaging appointment).

In act 310, an image processor reconstructs representations of the patient from the scan data. An object of the patient (e.g., anatomy) is reconstructed. The image processor reconstructs a representation for each scan (subset) of a series of scans acquired following the protocol.

For MR reconstruction, the k-space data is Fourier transformed into scalar values representing different spatial locations, such as spatial locations representing a plane through or volume of a region in the patient. Scalar pixel or voxel values are reconstructed as the MR image. The spatial distribution of measurements in object or image space is formed. This spatial distribution represents the object of the patient.

The reconstruction is performed, at least in part, using a machine-learned model, such as a neural network trained with deep machine learning. The machine-learned model is previously trained, and then used as trained in reconstruction for each of the subsets of the series of scans defined by the protocol. Fixed values of learned parameters are used for application. In application of the already trained network, the reconstruction process is followed. The machine-learned model is used in the reconstruction for each subset. In response to the input of the scan data for a given repetition for a given patient, a patient specific image is reconstructed. The machine-learned model may output the image as pixels, voxels, and/or a display formatted image in response to the input or be used in another way in the reconstruction. The learned values and network architecture, with any algorithms (e.g., extrapolation and gradient update) determine the output from the input.

The machine-learned model is designed to have an architecture for use with subsets. The architecture may be a neural network or other model trained to be used in separate reconstruction of different subsets, for reconstruction of a specific subset, and/or for combination of reconstructed subsets. Other adaptations for coupling information in training and/or application between subsets may be included in the architecture.

Since the machine-learned model and corresponding reconstruction may be performed on each scan or subset of the given protocol separately or independently, the reconstruction for each scan may be performed, at least in part, while another of the scans is occurring. For example, a scan image for one of the scans of the series of scans in the pulse sequence is reconstructed prior to completing scanning of another of the scans of the series, such as reconstructing the initial scan during the second scan of the series and prior to the third or later scans of the series.

The output of the reconstruction, such the output of the machine-learned model, is a two-dimensional distribution of pixels representing an area of the patient and/or a three-dimensional distribution of voxels representing a volume of the patient. The output from the last reconstruction iteration may be used as the output representation of the patient for a given subset.

Other processing may be performed on the input k-space measurements of the subset before input. Other processing may be performed on the output representation or reconstruction, such as spatial filtering, color mapping, and/or display formatting. In one embodiment, the machine-learned network outputs voxels or scalar values for a volume spatial distribution as the medical image. Volume rendering is performed to generate a display image. In alternative embodiments, the machine-learned network outputs the display image directly in response to the input.

The same object is reconstructed again from another subset. The spatial alignment and/or perspective may be different due to movement or shifting of the scan location in the patient or movement of the patient, but the same object is scanned in one or more subsequent subsets and reconstructed from the one or more subsequent subsets.

The same or different machine-learned model is used in reconstruction of the different subsets. The machine-learned model has an architecture designed for use with subsets, such as designed to reconstruct from a subset where the reconstruction is then later combined with other reconstructions from other subsets to form the output or final reconstruction. Due to this subset-based architecture, the machine-learned model may be used to reconstruct from a subset while the scanning for another subset occurs, such as reconstructing and outputting the reconstruction prior to completion of scanning for a subsequent or even temporally adjacent subset. The goal of enabling such separate reconstruction of subsets is accounted for in the design of the applied network or other machine-learned model.

There are dependencies between subsets since they all represent response from the same object. For a real-time reconstruction to match the quality of an offline approach, correlations with both the past and future subsets may be leveraged by coupling. In many cases, the machine-learned model architecture is designed to share information (e.g., to jointly process) between different subsets. For example, different subsets are stacked as an additional channel or dimension for input to the machine-learned model. In a real-time setting, the coupling instead uses side-information about the past, allowing reconstruction by subset. The multichannel approach is tied to the number of past subsets. In consequence, a new network is required for every new subset and the size of each network grows with the number of past subsets, resulting in an overall quadratic complexity in the number of subsets for both execution time and network parameters. By having the architecture instead be designed for separate reconstruction of subsets without direct input of other subsets, the real-time reconstruction or reconstruction with less noticeable delay (see FIG. 2) may be provided without the complexity of using multi-channel. Some multi-channel may be provided, such as where the model reconstructs from groups of subsets but less than all the subsets at a time.

In one embodiment, the subsets are reconstructed with the machine-learned model having an architecture for independent reconstruction. The same model is used for each subset, but a different model may be used for different subsets. For each subset, past information, information from other subsets, and information from the reconstruction of other subsets are not used in the reconstruction for the subset or group of subsets. Past information is not used.

Figure 4:
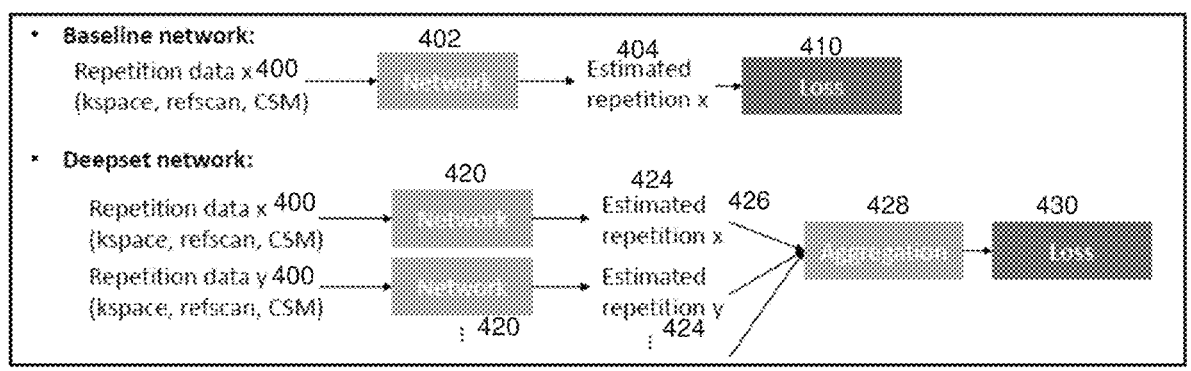
FIG. 4 illustrates example machine training of a network in a baseline approach of repetition-by-repetition and in an approach using aggregation across repetitions.

FIG. 4 shows an example. The baseline network approach receives the k-space data of one subset 400 at the input to the neural network 402 as the machine-learned model. The architecture of the network 402 was trained using the loss 410 to estimate the reconstruction 404 for just the one subset. Other input data may be included, such as a reference scan and coil sensitivity maps.

In another embodiment, information between subsets is coupled in the architecture through training. In application, the machine-learned model architecture is designed for separate and independent reconstruction of each subset. In training, information from multiple subsets are used. The machine-learned model used in reconstruction of one or more subsets was trained for the separate reconstruction using a loss based on aggregation across training subsets. In training, the images from different subsets of the protocol for which the network was trained are aggregated. The aggregation may be an average (e.g., sum), geometric mean, geometric product, or other combination used by a protocol. The aggregated image is compared to a ground truth image to determine the loss used in the optimization to find the values of the learnable parameters of the model.

The past or subset information is aggregated with a deepset network. One aggregated learnable function of the combination over all subsets couples through the one individual learnable function applied to each past subset. In such a method of training, the individual function is applied only once to each subset and added to the sum over the previous subsets, then the rest of the network runs in constant time, which results in overall linear complexity in the number of subsets. Such a method is appropriate if all past subsets are assumed to play similar roles (i.e., if there are no strong temporal dependencies in the data).

FIG. 4 shows an example coupling through training loss. The subsets 400 of different repetitions are input to the machine-learned model (e.g., network 420) for separate reconstruction of the representations 424. The representations are aggregated, forming the aggregation 428. The loss 430 for training the learnable parameters of the network 420 is based on comparison of this aggregation 428 across subsets, providing coupling in training and separate application by subset.

For application, information about future subsets will not be available at runtime so cannot be provided as an input to the reconstruction network. Where the training is performed offline, that information can be backpropagated through the loss during training following end-to-end training principles. Since every subset corresponds to a different observation of the same object, the final output of the study may not be every subset image but some final aggregate such as averaged images or parametric regressions. Computing the training loss on the final output of the different training samples lets each subset reconstruction be trained to be optimally combined with the future subsets.

In application, separate and independent reconstruction is provided for the different subsets. FIG. 4 shows two examples. In the baseline network, the network 402 is trained to perform separate processing of subsets without sharing information across subsets. In the deepset network, information between different subsets is coupled or shared during network training while still executing the network 420 as trained on single subsets 400.

The aggregation in training may include handcrafted processing steps such as motion or phase correction. In application, the reconstructed objects may be aggregated in the same way to form the final image, so motion correction, phase correction, or other handcrafted processing steps may be performed. For example, the reconstructions are spatially aligned 426 prior to aggregation. One of the reconstructions is spatially aligned 426 for motion correction relative to another reconstruction, and then the aligned reconstructions are combined.

Figure 5:
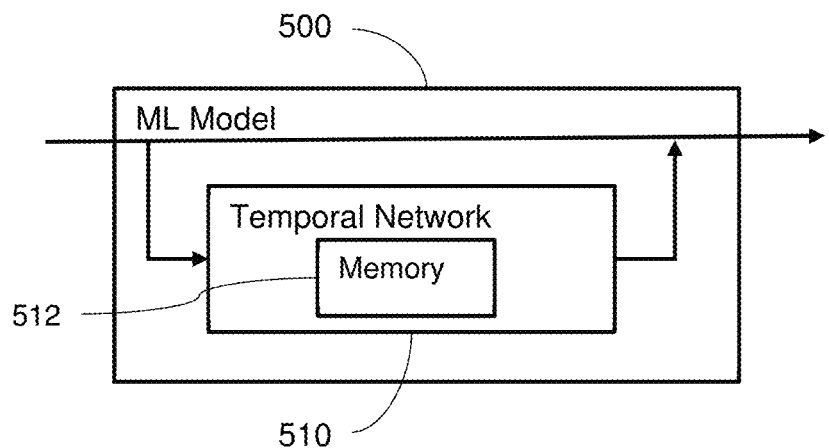
FIG. 5 illustrates an example architecture of a machine-learned model using a temporal network.

In other embodiments, information between subsets is provided as a coupling or sharing in application of the machine-learned model. In one approach, the architecture of the machine-learned model includes a temporal network. The temporal network relates one or more earlier subsets to the current subset. In training, the temporal network learns to extract relevant information from the history of reconstruction of earlier subsets of the scan. Example temporal networks include recurrent neural networks, gated recurrent units, or long-short term memories. FIG. 5 shows an example where the machine-learned model 500 includes a temporal network 510 with a memory 512. When a subsequent subset or data derived therefrom for reconstruction is input to the model 500, information from use of the model 500 for one or more previous subset reconstructions are provided by the temporal network 512 for creating the output of the model 500. In such an approach, the temporal network 510 learns to update its memory 510 with every new subset and provides the historical information to the reconstruction network of the model 500. This can be useful, for example, where past subsets become less relevant over time due to motion.

Figure 6:
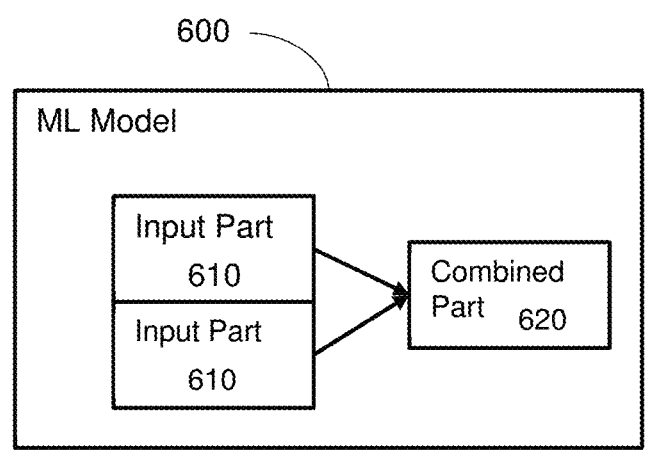
FIG. 6 illustrates an example architecture of a machine-learned model using different parts for different subsets.

In another approach coupling information in application of the model, the architecture includes different parts where one or more of the parts are used for the separate reconstruction of subsets and one or more parts perform reconstruction operations based on information from different subsets. FIG. 6 shows an example. The input part 610 includes layers, nodes, or other structure of the machine-learned model 600 that operates on information from one subset without information from another subset. Multiple such input parts 610 may be provided in a multi-channel approach or the same input part 610 is applied at different times for the different subsets. The reconstruction operations performed by the input part 610 may be performed for one subset while the other subset is still being acquired. The combined part 620 are layers, nodes, or other structure of the model 600 that use information from different subsets in a combined way to complete the reconstruction for the entire scan or for a subset of the subsets.

The model provides for multiple inputs (e.g., averages, repetitions, or other subsets) for which each input is first processed up to the point at which information from following acquisitions is needed. In the context of diffusion, images for different diffusion directions are often acquired, each with multiple averages or repetitions as subsets. The reconstruction of the final images is performed as two-step process. 1) reconstructing the different averages or repetitions for each direction. This can be, for example, the individual image reconstruction of a repetition or an RNN update. 2) Once images from all diffusion directions are available, these can be combined by the combined part to yield the final image. In other words, the architecture is split into parts, and the branches that can be processed without later inputs are identified. The final combination of the intermediate results can be conventional (e.g., not include trainable parameters) or also be a network.

Figure 7:
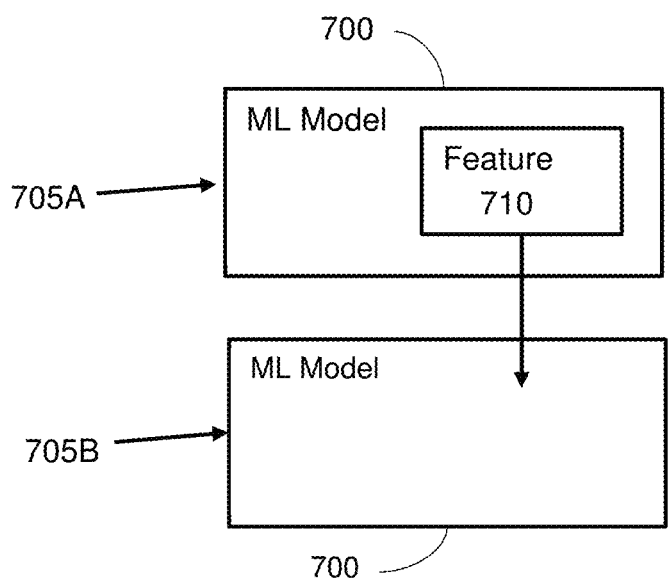
FIG. 7 illustrates an example architecture of a machine-learned model using information from one instance in reconstruction in another instance.

In yet another approach coupling information in application of the model, the architecture includes a conditional reconstruction model configured to receive historical information. FIG. 7 shows an example where the same machine-learned model 700 is shown being used for different subsets 705A, 705B, the top instance of the model 700 being for the earlier subset 705A. The machine-learned model 700 includes the conditional reconstruction model as a connection or memory for the feature 710. The historical information are values for one or more latent variables (i.e., features 710 in a neural network context) from application of the model 700 to a previous subset. For reconstruction for a current subset, the values from one or more reconstructions for a respective one or more previous subsets of the scan are used. The machine-learned model 700 uses values or other historical information for reconstructing from a current subset. Instead of values of latent features, the model 700 may use the output reconstruction or information derived therefrom for reconstruction for a current subset.

The machine-learned model 700 for separate reconstruction of individual or subset groups of subsets is designed as a conditional reconstruction model. The conditional reconstruction model is adapted based on contextual information extracted from history, if available. Initial application may use zero fill, no information, or default information for the history. Such contextual information can be sparse high-level features 710 output by deep-learned reconstruction models applied to previous inputs (e.g., averages or repetitions). High-level features contain rather general information about the object (e.g., larger shapes) which contrasts with low-level features (e.g., minor details such as lines or dots). Low-level features may be used in other embodiments. The reconstruction accounts for this additional information related to another subset.

Referring again to FIG. 3, the separate reconstructions of the subsets may be used to control the medical imaging system. Since representations from the subsets are available before completion of the scanning, the representations may be used to determine whether scanning to acquire additional subsets should continue or whether scanning should cease. One or more reconstructions from previously acquired subsets are used by the image processor to control the medical imaging system. The reconstruction pipeline adapts to provide feedback to the scanner to determine if other reconstructions (e.g., processing additional averages or repetitions) are still needed before generating the final image reconstruction to the user.

Different measures of quality or information content may be used. For example, the representations reconstructed from different subsets are compared. Where there is little motion and/or where similarity (e.g., correlation coefficient or minimum sum of absolute differences) is beyond a threshold level, then additional subsets may not be needed.

In act 330, the image processor generates an image of the object from the different reconstructions of the respective subsets. Pursuant to the protocol being used, the different reconstructions may be combined in act 340 to form a final image or representation of the object. The image processor combines the images into a final medical image. The reconstructions from the different scans are combined, such as using the aggregation approach provided by the protocol. For example, the representations (e.g., pixels or voxels) are averaged or summed as provided by diffusion-weighted or turbo-spin-echo protocols. The result is a medical image or representation of the patient from the scanning for that appointment or examination.

The combination occurs after or before any rendering or reformatting for display. The representation or data derived from the reconstructed representations are combined. For example, voxels are combined prior to rendering. The images in the form of voxels representing a volume are combined.

Other operations may be performed before, after, or during the combination. For example, spatial filtering is applied. As another example, the images are motion corrected or aligned spatially prior to combination.

The resulting combination representation or image is then rendered to a two-dimensional display. In act 350, a display (e.g., display screen or device) displays the medical image, such as the MR image formed by aggregation. The medical image, after or as part of any post processing, is formatted for display on the display. The display presents the image for viewing by the user, radiologist, physician, clinician, and/or patient. The image assists in diagnosis, prognosis, and/or therapy.

The displayed image may represent a planar region or area in the patient. Alternatively or additionally, the displayed image is a volume or surface rendering from voxels (three-dimensional distribution) to the two-dimensional display.

The final image based on combination from all or selected subsets is displayed in an amount of time after completion of the scanning of the last subset that is less than a time to reconstruct from all the used subsets. Referring to FIG. 2, the data acquisition 200 ends at a given time. The reconstruction 210 ends shortly thereafter, such as within 1-10 seconds to finish already begun reconstruction and aggregate. Rather than causing noticeable delay of 30 or more seconds to perform the entire reconstruction 210 after ceasing the scanning or acquisition 200, most of the reconstruction 210 is performed while still scanning or acquiring 200. The design of the machine-learned model enables reconstruction 210 during acquisition 200. Therefore, the time spent during acquisition (e.g., often several minutes) can be used for image reconstruction. If reconstruction time for one subset is smaller than acquisition time of one subset, the overall "visible" reconstruction time is only the reconstruction time of a single (last) subset ("real-time reconstruction").

The machine-learned model is trained for application. The training data includes many sets of data, such as k-space data in sets where each set include multiple subsets from a same scan sequence or protocol. Tens, hundreds, or thousands of sample scan data are acquired, such as from scans of volunteers or patients, scans of phantoms, simulation of scanning, and/or by image processing to create further samples. Many examples that may result from different scan settings, patient anatomy, scanner characteristics, or other variance that results in different samples in scanning are used. In one embodiment, an already gathered or created MR dataset is used for the training data. The samples are for scanning following a protocol that uses subsets, such as samples from diffusion-weighted, contrast (e.g., different echo times or flip angles), and/or turbo-spin-echo imaging. Depending on the role in reconstruction of the model to be machine trained, the training data may use k-space data or image domain data for the samples. The samples are used in machine learning (e.g., deep learning) to determine the values of the learnable variables (e.g., values for convolution kernels) that produce outputs with minimized cost or loss across the variance of the different samples. The training data includes ground truth information, such as desired subset reconstructions or an aggregate image. The desired representation or image resulting from a given sample is provided as the ground truth.

A computer (e.g., image processor) machine trains the model for reconstruction, such as training for a neural network for regularization, gradient, or k-space to final image operations. The neural network is machine trained for reconstruction using the training data, including many input samples of sets of scan data repetitions and corresponding ground truth outputs. In one embodiment, deep learning is used to train the model. The training learns both the features of the input data and the conversion of those features to the desired output (i.e., denoised or regularized image domain data). Backpropagation, RMSprop, ADAM, or another optimization is used in learning the values of the learnable parameters of the network (e.g., the convolutional neural network (CNN) or fully connection network (FCN)). Where the training is supervised, the differences (e.g., L1, L2, mean square error, or other loss) between the estimated output and the ground truth output are minimized.

Any architecture or layer structure for machine learning to perform an operation for separately reconstructing from subsets may be used. For example, any of the architectures discussed for FIGS. 4-7 may be used. The architecture defines the structure, learnable parameters, and relationships between parameters. In one embodiment, a convolutional or another neural network is used. Any number of layers and nodes within layers may be used. A DenseNet, U-Net, encoder-decoder, Deep Iterative Down-Up CNN, and/or another network may be used. Some of the network may include dense blocks (i.e., multiple layers in sequence outputting to the next layer as well as the final layer in the dense block). Any know known or later developed neural network may be used. Any number of hidden layers may be provided between the input layer and output layer. For iterative reconstruction, the architecture may include an unrolled arrangement of layers or iterative optimization.

The same network is trained to be used for all the subsets. Alternatively, a different network is provided for each subset. A different architecture or same architecture but with different values for one or more of the learnable parameters of the network may be used for each subset. Different networks are trained for reconstruction for different subsets.

Machine learning is an offline training phase where the goal is to identify an optimal set of values of learnable parameters of the model that can be applied to many different inputs. These machine-learned parameters can subsequently be used during clinical operation to reconstruct. Once learned, the machine-learned model is used in an online processing phase in which scan data from multiple subsets for a given patient scan are reconstructed into an image or images. Once trained, the machine-learned model is applied in reconstruction of a representation or image of a patient from a scan of that patient.

Although the subject matter has been described in terms of exemplary embodiments, it is not limited thereto. Rather, the appended claims should be construed broadly, to include other variants and embodiments, which can be made by those skilled in the art.

What is claimed is:

1. A method of reconstruction for a medical imaging system, the method comprising:
scanning, using a plurality of repetitions of a pulse sequence, a patient by the medical imaging system without the patient leaving the medical imaging system, the scanning acquiring in sequence at least a first subset of data using a first repetition of the plurality of repetitions of the pulse sequence and a second subset of data using a second repetition of the plurality of repetitions;
first reconstructing, after the first repetition is complete and during a same time period as when the second repetition of the scanning by the medical imaging system is performed, a first partial representation of an object of the patient from the first subset of the scan data, the first reconstructing being by, at least in part, a machine-learned model, the machine-learned model having an architecture for separate reconstruction of the first subset of data and the second subset of data;
second reconstructing, after the second repetition acquires the second subset of data, a second partial representation of the object from the second subset of the scan data, the second reconstruction being by, at least in part, the machine-learned model; and
generating an image of the object from the first partial representation and the second partial representation.

2. The method of claim 1 wherein scanning comprises magnetic resonance scanning pursuant to a diffusion-weighted, turbo-spin-echo, contrast with different echo times, contrast with different flip angles, contrast with different b-values, or contrast with different averages protocol.

3. The method of claim 1 wherein scanning comprises scanning with the first and second subsets being temporally adjacent subsets where the scanning includes three or more subsets, and wherein the first reconstructing completes prior to the completion of the scanning for the second subset.

4. The method of claim 1 wherein scanning comprises scanning the patient pursuant to a protocol for a single imaging appointment.

5. The method of claim 1 wherein the first reconstructing and the second reconstructing comprise first reconstructing and second reconstructing where the architecture independently reconstructs for the first subset and the second subset.

6. The method of claim 1 wherein the first reconstructing and the second reconstructing comprise first reconstructing and second reconstructing where the machine-learned model was trained for separate reconstruction using a loss based on aggregation across training subsets.

7. The method of claim 6 wherein generating the image comprises motion correcting one of the first partial representation and the second partial representation relative to the other and combining the first partial representation and the second partial representation as motion corrected.

8. The method of claim 1 wherein the first reconstructing and the second reconstructing comprise first reconstructing and second reconstructing by an architecture that includes a temporal network relating the first subset to the second subset.

9. The method of claim 8 wherein second reconstructing comprises second reconstructing where the temporal network comprises a recurrent neural network, a gated recurrent unit, or a long-short term memory.

10. The method of claim 1 wherein the first reconstructing and the second reconstructing comprise first reconstructing and second reconstructing with an architecture that includes different parts where one or more of the parts are performed for the first reconstructing without the second subset and one or more parts are performed after acquiring the second subset.

11. The method of claim 1 wherein the first reconstructing and the second reconstructing comprise first reconstructing and second reconstructing where the architecture comprises a conditional reconstruction model configured to receive historical information.

12. The method of claim 11 wherein the historical information comprises values for latent variables from application of the machine-learned model to a previous subset such that the machine-learned model uses the values from the first reconstructing for the second reconstructing.

13. The method of claim 1 further comprising controlling the medical imaging system to cease scanning based on the second reconstruction.

14. The method of claim 1 wherein generating the image comprises displaying the image in an amount of time after completion of the scanning to acquire the second subset that is less than a time to reconstruct from both the first and second subsets.

15. A system for reconstruction in medical imaging, the system comprising:
a medical scanner configured to scan a region of a patient using a plurality of repetitions of a pulse sequence, the scan providing at least a first subset of data using a first repetition of the plurality of repetitions of the pulse sequence and a second subset of data using a second repetition of the plurality of repetitions;
an image processor configured to reconstruct a representation of the region separately for each of the first subset and the second subset, the image processor configured to reconstruct a first partial representation by application of a machine-learned model to the first subset while the medical scanner is scanning the region of the patient with the second repetition to acquire the second subset, the machine-learned model using information from a previous reconstruction in a later reconstruction; and a display configured to display an image of the region from a combination of the first partial representation with further representations from subsequent repetitions including at least the second repetition.

16. The system of claim 15 wherein the machine-learned model includes a temporal network, the temporal network using the information.

17. The system of claim 15 wherein the machine-learned model includes inputs for the subsets and includes a part combining the information.

18. The system of claim 15 wherein the information comprises values of latent variables of the previous reconstruction.

19. The system of claim 15 wherein the scan is a contrast, diffusion-weighted, or turbo-spin-echo magnetic resonance scan.

20. A system for reconstruction in medical imaging, the system comprising:

a medical scanner configured to repeatedly scan a region of a patient using a plurality of repetitions of a pulse sequence, the scan providing at least a first subset of data using a first repetition of the plurality of repetitions of the pulse sequence and a second subset of data using a second repetition of the plurality of repetitions;

an image processor configured to reconstruct a representation of the region separately for each of the first subset of data and the second subset of data, the image processor configured to reconstruct by application of a machine-learned model where the representation for one of the first subset of data or the second subset of data is reconstructed prior to completion of the scan for another of the first subset of data or the second subset of data; and a display configured to display an image of the region from a combination of the representations from the different subsets.

* * * * *